(12) United States Patent
Singh et al.

(10) Patent No.: US 6,896,890 B2
(45) Date of Patent: May 24, 2005

(54) OIL-IN-WATER EMULSION FORMULATION CONTAINING FREE AND ENTRAPPED HYDROQUINONE AND RETINOL

(75) Inventors: B. Sandhya Singh, Bedminister, NJ (US); Subhash J. Saxena, Bedminister, NJ (US); Marie-Helen Beausoleil, Issy-les-Moulineaux (DE)

(73) Assignee: R.P. Scherer Technologies, Inc., Las Vegas, NV (US)

( * ) Notice: Subject to any disclaimer, the term of this patent is extended or adjusted under 35 U.S.C. 154(b) by 317 days.

(21) Appl. No.: 10/151,600

(22) Filed: May 16, 2002

(65) Prior Publication Data

US 2003/0032680 A1 Feb. 13, 2003

Related U.S. Application Data

(63) Continuation-in-part of application No. 09/565,321, filed on May 5, 2000, now abandoned.

(51) Int. Cl.$^7$ ............................................. A61K 7/00
(52) U.S. Cl. .................. 424/401; 424/489; 514/844; 514/938; 514/951; 514/772.3
(58) Field of Search ............................... 424/401, 489, 424/484, 78.03

(56) References Cited

U.S. PATENT DOCUMENTS 5,851,538 A * 12/1998 Froix et al. .................. 424/401
5,976,555 A * 11/1999 Liu et al. ..................... 424/401

* cited by examiner

*Primary Examiner*—James M. Spear
(74) *Attorney, Agent, or Firm*—Donald O. Nickey

(57) ABSTRACT

An oil-in-water emulsion formulation containing hydroquinone and retinol, which comprises an oil-in-water emulsion containing free hydroquinone, hydroquinone entrapped in absorbent micro-agglomerates and/or impregnated in porous microparticles; and retinol-impregnated microparticles.

21 Claims, No Drawings

OIL-IN-WATER EMULSION FORMULATION CONTAINING FREE AND ENTRAPPED HYDROQUINONE AND RETINOL

RELATED APPLICATIONS

This application is a continuation-in-part of application Ser. No. 09/565,321 filed May 5, 2000, now abandoned.

BACKGROUND OF THE INVENTION

1. Field of the Invention

This invention relates to an oil-in-water emulsion formulation containing hydroquinone and retinol. More specifically this invention relates to oil-in-water emulsions that contain hydroquinone entrapped in micro-agglomerates and/ or impregnated in porous microparticles and in free form; and retinol-impregnated porous microparticles.

2. Background to the Invention

Hydroquinone is a reduced quinone, well-recognized as an efficacious skin-lightening agent. When topically applied, it produces a reversible depigmentation of the skin by inhibiting the enzymatic oxidation of tyrosine to 3,4-dihydroxyphenylalanine, as well as suppressing other metabolic processes of melanocytes. In a clinical setting, hydroquinone is employed to treat hypermelanosis. It has likewise been utilized to bleach hyperpigmented skin conditions including chloasma, melasma, freckles, and senile lentigines. Hydroquinone is available in over-the-counter and prescription products. Although hydroquinone is considered a mild irritant, it displays minimal toxicity in humans.

Retinol, along with other retinoids, has enjoyed increasing popularity as an active ingredient in skin care compositions, especially for photoaging and sun damage. However, more so than other retinoids, retinol tends to decompose on exposure to light, heat, and oxygen. The problem of decomposition has been addressed to some extent by formulating retinol with antioxidants and chelating agents, and storing it in opaque or colored containers, and several patents and published applications, for example, PCT International Application Publication No. WO 93/00085 and European Patent Application Publication Nos. 0 440 398 and 0 596 106, all to Johnson & Johnson, describe water-in-oil emulsions containing retinol, which are asserted to be stable. U.S. Pat. No. 5,891,740 to Rinaldi et al. discloses soft capsule fill formulations containing retinol. The fill material for the '740 patent may be optionally thickened with silicone oil, or may be an emulsion comprising a silicon oil. Ascorbic acid may be present as ascorbic acid-impregnated microparticles and or within the emulsion. This patent makes no disclosure nor suggestion of hydroquinone in separate microparticles or micro-agglomerates, and no disclosure of an oil-in-water emulsion containing them together with retinol-impregnated microparticles.

U.S. Pat. No. 5,851,538, discloses an oil-in-water emulsion containing retinol. Further, this reference discloses oil-in-water emulsions containing the retinoids in microporous microspheres. Retinol and melanin are impregnated one after the other into the same microspheres and then the microspheres are used in the oil-in-water emulsion. There is no disclosure nor suggestion in the '538 patent of hydroquinone in separate microparticles or micro-agglomerates, and no disclosure of an oil-in-water emulsion containing them together with retinol-impregnated microparticles. Most importantly, this reference makes no suggestion of having some free hydroquinone in the emulsion to keep the loaded hydroquinone from coming out of the porous carriers and provide some immediate therapeutic benefit. Lastly, the inclusion of some small level of free hydroquinone reduces the "powder load" on the final emulsion and thereby produces an improved product.

The disclosures of these and other documents referred to in this application are incorporated herein by reference.

It would be of value to have a stable oil-in-water emulsion formulation containing both hydroquinone and retinol as dermatologists are constantly searching for improved formulations that provide a desired therapeutic effect.

BRIEF SUMMARY OF THE INVENTION

In a first aspect, this invention provides an oil-in-water emulsion formulation containing hydroquinone and retinol, comprising:
(i) an oil-in-water emulsion containing at least 0.01% by weight of free hydroquinone;
(ii) separately dispersed within the oil-in-water emulsion,
  (a) one or both of hydroquinone entrapped in micro-agglomerates and hydroquinone-impregnated porous microparticles; and
  (b) retinol-impregnated porous microparticles.

In a second aspect, this invention provides a method of application of hydroquinone and retinol to the skin, comprising the administration of the formulation of the first aspect of this invention.

A third aspect of the invention, relates to the discovery that hydroquinone entrapped in micro-agglomerates and impregnated in porous microparticles has increased stability and the presence of a small level of free hydroquinone provides immediate therapeutic benefit and further enhances the stability of the hydroquinone by preventing its premature release from the micro-agglomerates and/or porous microparticles.

As used herein, the term "free hydroquinone" means hydroquinone that is present in the oil-in-water emulsion that is not entrapped in micro-agglomerates or impregnated in porous microparticles.

As used herein and in the claims, the phrase "total hydroquinone content" means the total hydroquinone contained within the oil-in-water emulsion that is from the free hydroquinone and from the hydroquinone entrapped in micro-agglomerates and hydroquinone impregnated porous microparticles. The formulation according to the present invention has total hydroquinone content of the emulsion from about 0.01% to about 10% by weight. More preferably, the oil-in-water emulsion has a total hydroquinone content from about 0.1% to about 5% by weight.

DETAILED DESCRIPTION OF THE INVENTION

According to the first aspect of this invention, there are obtained oil-in-water emulsion formulations for hydroquinone and retinol, in which the hydroquinone is present in free form, entrapped in absorbent micro-agglomerates or as hydroquinone-impregnated porous microparticles and the retinol is present as retinol-impregnated porous microparticles. Thus, the invention comprises a formulation in which hydroquinone and retinol are can act in concert upon topical application, but are sequestered from one another in the formulation. The presence of free hydroquinone improves the stability of the impregnated hydroquinone and also provides for immediate therapeutic relief. Formulations according to this invention are stable and topically cosmetically acceptable, thereby providing attractive forms for the topical delivery of hydroquinone and retinol.

According to the second aspect of this invention, a method of applying hydroquinone and retinol to the skin is provided, the method comprising the administration of the formulation of the first aspect of the invention.

Number ranges given in the specification, such as size ranges and the like, should be considered approximate, unless specifically stated.

Ingredient names are taken from the *International Cosmetic Ingredient Dictionary and Handbook*, 8th edition, 2000, Cosmetic, Toiletry, and Fragrance Association, Washington, D.C.

The Micro-Agglomerates

Suitable micro-agglomerates for this invention are solid, water-insoluble micro-agglomerates of submicron-sized solid polymeric particles. Micro-agglomerates of this type, and methods of their preparation, are disclosed in U.S. Pat. Nos. 4,962,133 and 4,962,170 (both to Chromecek et al.) and references cited therein.

The micro-agglomerates of the invention form an ultralight powder that can adsorb liquids without changing the free-flowing nature of the powder as a whole. The powder is composed of a lattice of solid, submicron-sized, generally elliptical or spherical, unit particles ranging from about 0.1 $\mu$m to about 0.5 $\mu$m, typically about 0.3 $\mu$m, in diameter. The powder also consists of micro-agglomerates of fused unit particles of sizes in the range of 10 $\mu$m to 80 $\mu$m in average diameter, and aggregates of these fused micro-agglomerates of sizes in the range of from about 200 $\mu$m to about 1200 $\mu$m in average diameter. The unit particles themselves do not have any significant porosity, and the micro-agglomerates absorb liquids primarily through filling of interstitial voids by capillary action. The powder has a bulk density from less than 0.1 g/mL to about 0.3 g/mL. In this form, the powder has the capacity to adsorb several times its own weight of liquids (including melted solids).

The micro-agglomerates are composed of organic polymers and are formed by precipitation polymerization of a mixture of monoethylenically unsaturated and polyethylenically unsaturated monomers in a suitable solvent, as described in the patents listed above. Monoethylenically unsaturated monomers suitable for forming micro-agglomerates for use in this invention include styrene, ethylvinylbenzene, vinyltoluene, acrylic acid and its esters, such as ethyl acrylate, methacrylic acid and its esters, such as methyl methacrylate and lauryl methacrylate, vinyl esters, such as vinyl acetate, vinyl propionate, vinyl stearate, and vinyl laurate, vinylic ketones, such as vinyl methyl ketone and methyl isopropenyl ketone, and vinyl ethers, such as vinyl methyl ether, and the like. Polyethylenically unsaturated monomers suitable for forming micro-agglomerates for use in this invention include divinylbenzene, divinyl ketone, divinyl sulfone, polyvinyl or polyallyl esters of dibasic or polybasic acids, such as divinyl sebacate, diallyl adipate, diallyl phthalate, diallyl sebacate, polyvinyl or polyallyl ethers of diols or polyols, such as ethylene glycol divinyl ether and diethylene glycol diallyl ether, polyacrylate or polymethacrylate esters of diols or polyols, such as ethylene glycol dimethacrylate, polyethylene glycol diacrylate, trimethylolpropane trimethacrylate, and the like. Typically the monoethylenically unsaturated monomer will be present at from 20% to 80% of the monomer mixture, with the polyethylenically unsaturated monomer forming the remainder of the mixture. Preferred monomer mixtures include styrene/divinylbenzene, vinyl stearate/divinylbenzene, methyl methacrylate/ethylene glycol dimethacrylate, and lauryl methacrylate/ethylene glycol dimethacrylate.

The mixture of monomers, together with a low-boiling organic solvent, such as isopropanol, and a polymerization catalyst, such as a peroxide, are stirred to form a solution. On heating and continuous stirring, the monomers polymerize to form solid microparticles, which agglomerate into micro-agglomerates. The micro-agglomerates are then filtered, washed with a volatile organic solvent such as isopropanol to remove unreacted monomers, and, finally, dried under vacuum to afford absorbent micro-agglomerates.

In one method of preparation of the absorbent micro-agglomerates of the invention, lauryl methacrylate and ethylene glycol dimethacrylate are added to heated isopropanol. A catalyst is added under mixing, and the mixture is sparged with nitrogen. The reaction is allowed to complete under heating, and the resultant mixture is filtered and washed with isopropanol. The "wet cake" is blended and dried to a specified residual isopropanol content.

Micro-agglomerates of this type are commercially available under the trademark POLYTRAP® from Enhanced Derm Technologies, Inc. of Redwood, Calif.

The Porous Microparticles

Suitable porous microparticles for this invention are solid, water-insoluble, polymeric microparticles having a network of interconnected pores open to the particle surface, providing substantially full communication between the internal pore space and the particle exterior surface. Microparticles of this type, and methods for their preparation, are disclosed in U.S. Pat. No. 4,690,825 (Won), U.S. Pat. No. 4,873,091 (Jankower et al.), U.S. Pat. No. 5,073,365 (Katz et al.), U.S. Pat. No. 5,135,740 (Katz et al.), and U.S. Pat. No. 5,145,675 (Won).

The porous microparticles are generally spherical in shape and have a weight average diameter from less than 1 $\mu$m to about 500 $\mu$m or more, particularly from about 5 $\mu$m to about 100 $\mu$m, more particularly from about 10 $\mu$m to about 50 $\mu$m, especially about 20 $\mu$m. The pore dimensions within the microparticles may vary, with optimum dimensions depending on the polymers used to form the microparticles and the diffusive characteristics of the material to be impregnated. Typical pore volumes are from about 0.01 $cm^3/g$ to about 4 $cm^3/g$, particularly from about 0.1 $cm^3/g$ to about 2 $cm^3/g$; typical surface areas are from about 1 $m^2/g$ to about 500 $m^2/g$, particularly from about 20 $m^2/g$ to about 350 $m^2/g$; and typical pore diameters are from about 0.0001 $\mu$m to about 3 $\mu$m, particularly from about 0.003 $\mu$m to about 1 $\mu$m. The average diameter of the microparticles may be determined by sedimentation or by a laser microsizer; the pore volume may be determined by mercury intrusion; and the surface area may be determined by nitrogen adsorption (the BET method).

The porous microparticles are composed of organic polymers and are formed by suspension polymerization of a mixture of monoethylenically unsaturated and polyethylenically unsaturated monomers in the presence of a porogen (a pore-forming agent), as described in the patents listed above. Monoethylenically unsaturated monomers suitable for forming microparticles for use in this invention include styrene, ethylvinylbenzene, vinyltoluene, acrylic acid and its esters, such as ethyl acrylate, methacrylic acid and its esters, such as methyl methacrylate and lauryl methacrylate, vinyl esters, such as vinyl acetate, vinyl propionate, vinyl stearate, and vinyl laurate, vinylic ketones, such as vinyl methyl ketone and methyl isopropenyl ketone, and vinyl ethers, such as vinyl methyl ether, and the like. Polyethylenically unsaturated monomers suitable for forming microparticles for use in this invention include divinylbenzene, divinyl ketone, divinyl sulfone, polyvinyl or polyallyl esters of dibasic or polybasic acids, such as divinyl sebacate, diallyl adipate, diallyl phthalate, diallyl sebacate, polyvinyl or polyallyl ethers of diols or polyols, such as ethylene glycol divinyl ether and diethylene glycol diallyl ether, polyacrylate or polymethacrylate esters of diols or polyols, such as ethylene glycol dimethacrylate, polyethylene glycol diacrylate, trimethylolpropane trimethacrylate, and the like. Typically the monoethylenically unsaturated monomer will be present at from 20% to 80% of the monomer mixture, with the polyethylenically unsaturated monomer forming the remainder of the mixture. Preferred monomer mixtures include styrene/divinylbenzene, vinyl stearate/divinylbenzene, methyl methacrylate/ethylene glycol dimethacrylate, and lauryl methacrylate/ethylene glycol dimethacrylate.

The mixture of monomers, together with the porogen, which is typically a moderately low-boiling hydrocarbon such as heptane or toluene, and a polymerization catalyst, such as a peroxide, are added to an aqueous phase, typically containing a dispersant, and stirred to form a suspension of the organic phase in the aqueous phase with droplets of the desired size of the resulting particles. On heating and continued stirring, the monomers polymerize to form solid porous microparticles having the pores filled with the porogen. The microparticles are filtered, washed with water to remove the dispersants and then with volatile organic solvents such as isopropanol to remove unreacted monomers and the porogen, and then dried under vacuum to afford the porous microparticles.

Microparticles of this type are commercially available from Enhanced Derm Technologies, Inc. under the trademark MICROSPONGE®.

The Hydroquinone Entrapped in Micro-Agglomerates

Hydroquinone entrapped in micro-agglomerates suitable for use in this invention may be prepared by mixing micro-agglomerates with a solution containing hydroquinone and subsequently removing the solvent. Typically, the hydroquinone-loaded micro-agglomerates will have a hydroquinone content from 1% to 80%, particularly from 20% to 70%, especially around 60%, by weight of the loaded micro-agglomerates.

Even when enloaded into micro-agglomerates or impregnated into porous microparticles, a very small level of free hydroquinone is left on the outside of the particles. It is typical for the particles to contain up to 2% by weight of free hydroquinone. In one embodiment of the invention, at least 0.01 weight percent of the total emulsion formulation should be free hydroquinone. This is especially so with oil-in-water emulsions that contain more than 2 weight percent hydroquinone entrapped in the micro-agglomerates and/or impregnated porous microparticles. When the weight composition of the hydroquinone is increased to about 4 weight percent, it has been found to be advantageous to place 2.5 weight percent hydroquinone in the impregnated porous microparticles and/or entrapped in micro-agglomerates with about 1.5% by weight in the form of free hydroquinone contained within the emulsion.

One additional aspect of the present invention is that the use of hydroquinone in free-form reduces what is known as the "powder load" on the emulsion. Powder load is a term used to describe lotions and creams that have an excessive amount of powder in their composition. This sometimes causes great difficulty in preparing an acceptable product for topical application to the skin. The presence of the free hydroquinone is also effective in keeping the hydroquinone entrapped in the micro-agglomerates and/or impregnated in the porous microparticles from escaping prior to topical application. The pre-saturation of the vehicle (i.e. the oil-in-water emulsion) reduces the amount of hydroquinone escaping from the particles prior to topical application.

The hydroquinone composition may contain additional ingredients. Typical optional additional ingredients in the hydroquinone composition include antioxidants. Both water-soluble and oil-soluble antioxidants may be used. Examples of water-soluble antioxidants include ascorbic acid and its salts, such as sodium ascorbate, isoascorbic acid and its salts, sodium sulfite, sodium metabisulfite, sodium thiosulfite, thiols such as thioglycerol, thiosorbitol, thiourea, thioglycolic acid, and cysteine, and the like. Examples of oil-soluble antioxidants include BHT (butylated hydroxytoluene), BHA (butylated hydroxyanisole), tocopherol (vitamin E), tocopheryl acetate, ascorbyl palmitate, hydroquinone, di-t-butylhydroquinone, propyl gallate, and the like. The amount of antioxidant may vary, and is not critical to this invention provided that sufficient is present to give the hydroquinone the desired stability. In most applications, an amount ranging from 0.01% to 10% by weight of the hydroquinone composition will be appropriate.

Other optional ingredients in the hydroquinone composition include chelating agents such as EDTA (ethylenediaminetetraacetic acid) and its salts, for example disodium EDTA, trisodium NTA (nitrilotriacetic acid), etidronic acid and its salts, sodium dihydroxyethylglycinate, citric acid and its salts, and the like. The amount of chelating agent may likewise vary and is not critical to this invention; and in most applications, an amount ranging from 0.01% to 1% by weight of the hydroquinone composition is sufficient.

Typically, the hydroquinone and any additional ingredients are dissolved in a volatile organic solvent, such as a lower alcohol or lower ketone, for example isopropanol, and the solution mixed with the micro-agglomerates, so that the solution is absorbed into the interstitices of the lattice. Once the micro-agglomerates have absorbed the solution, the solvent is removed by evaporation, typically under reduced pressure and optionally with mild heating, avoiding excessive temperatures that may speed decomposition or oxidation of the hydroquinone. This process may be repeated one or more times to increase the hydroquinone loading of the micro-agglomerates.

Because of the sensitivity of hydroquinone to oxygen, the hydroquinone and all formulations containing it will typically be handled in an oxygen-free atmosphere, e.g. under nitrogen or other inert gas. Solvents will typically be degassed and/or purged with nitrogen before use, formulations and intermediate formulations degassed, and storage containers purged with nitrogen both before and after filling with a hydroquinone-containing formulation, such as hydroquinone-loaded micro-agglomerates and compositions containing hydroquinone.

The Hydroquinone-Impregnated Porous Microparticles

Hydroquinone-impregnated porous microparticles suitable for use in this invention may be prepared by mixing the porous microparticles with a solution containing hydroquinone and subsequently removing the solvent. Typically, the hydroquinone-impregnated porous microparticles will have a hydroquinone content from about 1% to about 80%, particularly from about 20% to about 70%, especially around 60% by weight of the impregnated microparticles; and may contain an overage of hydroquinone (up to about 20%) to ensure adequate potency after storage.

The hydroquinone may be entrapped in the micro-agglomerates as a hydroquinone composition containing additional ingredients, as mentioned above for the micro-agglomerates.

Typically, the hydroquinone (hydroquinone blend) will be dissolved in a volatile organic solvent, such as a lower alcohol or lower ketone, for example isopropanol or acetone, and the solution mixed with the microparticles so that the solution is absorbed into the pores of the microparticles. Once the microparticles have absorbed the solution, the solvent is removed by evaporation, typically under reduced pressure and optionally with mild heating, avoiding excessive temperatures that may speed decomposition or oxidation of the hydroquinone.

Because of the sensitivity of hydroquinone to oxygen, the hydroquinone and all formulations containing it will typically be handled in an oxygen-free atmosphere, e.g. under nitrogen or other inert gas. Solvents will typically be degassed and/or purged with nitrogen before use, emulsions and intermediate formulations degassed, and storage containers purged with nitrogen both before and after filling with a hydroquinone-containing formulation, such as the hydroquinone-impregnated porous microspheres and emulsions containing hydroquinone.

The Retinol-Impregnated Porous Microparticles

Retinol-impregnated porous microparticles suitable for use in this invention may be prepared by mixing the porous microparticles with a solution containing retinol and subsequently removing the solvent. Typically, the retinol-impregnated porous microparticles will have a retinol content from about 1% to about 50%, particularly from about 10% to about 30%, especially around 20% by weight of the impregnated microparticles; and usually contain an overage of retinol (up to about 20%) to ensure adequate potency after storage.

The retinol is preferably impregnated into the porous microparticles as a retinoid composition containing additional ingredients, such as antioxidants and chelating agents. Typically, the retinoid composition will comprise from about 5% to about 95% by weight of retinol, more typically, from about 10% to about 70% by weight of retinol. Frequently, the retinol will be a commercial retinol blend, containing an antioxidant, such as butylated hydroxytoluene, and a dispersant, such as polysorbate 20, in addition to the retinol; and additional ingredients will be added to that retinol blend.

Typical optional additional ingredients in the retinoid composition include antioxidants. Both water-soluble and oil-soluble antioxidants may be used. Examples of water-soluble antioxidants include ascorbic acid and its salts, such as sodium ascorbate, isoascorbic acid and its salts, sodium sulfite, sodium metabisulfite, sodium thiosulfite, thiols such as thioglycerol, thiosorbitol, thiourea, thioglycolic acid, and cysteine, and the like. Examples of oil-soluble antioxidants include BHT, BHA, tocopherol, tocopheryl acetate, ascorbyl palmitate, propyl gallate, and the like. The amount of antioxidant may vary, and is not critical to this invention provided that sufficient is present to give the retinol the desired stability. In most applications, an amount ranging from about 0.0001% to about 10% by weight of the retinoid composition will be appropriate.

Other optional ingredients in the retinoid composition include chelating agents such as EDTA and its salts, for example disodium EDTA, trisodium NTA, etidronic acid and its salts, sodium dihydroxyethylglycinate, citric acid and its salts, and the like. The amount of chelating agent may likewise vary and is not critical to this invention; and in most applications, an amount ranging from about 0.01% to about 1% by weight of the retinoid composition is sufficient.

Typically, the retinol (retinol blend) will be dissolved in a volatile organic solvent, such as a lower alcohol or lower ketone, for example isopropanol or acetone, and the solution mixed with the microparticles so that the solution is absorbed into the pores of the microparticles. Once the microparticles have absorbed the solution, the solvent is removed by evaporation, typically under reduced pressure and optionally with mild heating, avoiding excessive temperatures that may speed decomposition or oxidation of the retinol.

Because of the sensitivity of retinol to light, especially ultraviolet light, heat, and oxygen, the retinol and all formulations containing it will typically be handled under yellow light, and in opaque or colored containers, and an oxygen-free atmosphere, e.g. under nitrogen or other inert gas. Solvents will typically be degassed and/or purged with nitrogen before use, emulsions and intermediate formulations degassed, and storage containers purged with nitrogen both before and after filling with a retinol-containing formulation, such as the retinol-impregnated porous microspheres and emulsions containing retinol.

Oil-in Water Emulsions

The oil-in-water emulsions of the invention comprise lipophilic (oil) droplets in a continuous hydrophilic (water) phase. These emulsions may comprise some 10–40% oil phase and 60–90% water phase. The water phase may contain humectants, which prevent the desiccation and consequent hardening of the emulsions. Oil-in-water emulsions of the invention may typically contain, but are not limited to, polyoxyethylene alcohol (varying in the fatty alcohol and in the degree of polymerization of polyethylene glycol), aryl alcohol, wax, silicone oil, mineral oil, deionized water, glycerol, and additional emulsifying, thickening, and preservative agents. Emulsifiers constitute an important component of the formulations, as they lend to the stability of the emulsion as a whole by coating the oil droplets. Emulsifiers are, essentially, surfactants. These surfactants can be ionic or non-ionic, and they can be used alone or in admixture. They include cetearyl alcohol and sodium cetearyl sulfate, PEG-1000 monocetyl ether, or quaternary ammonium salts such as alkyl trimethyl ammonium bromide; likewise, the polyol ester glycerol monostearate and potassium stearate, sodium lauryl sulfate, and ethoxylated fatty alcohols constitute good co-emulsifiers. Fatty acids like stearic acids may be included to regulate the consistency of the emulsion. Finally, polymers such as carbomers can be included in small amounts to stabilize the emulsion.

The oil-in-water emulsion of the invention contains free hydroquinone and (1) one or both of hydroquinone entrapped in micro-agglomerates and hydroquinone-impregnated porous microparticles, and (2) retinol-impregnated porous microparticles. Typically, the resulting formulation will have a free hydroquinone content of at least 0.01% by weight, total hydroquinone is at least 0.1%, more particularly at least 1%; and less than 10%, particularly less than 5%. A retinol content of at least 0.0001%, particularly at least 0.01%, more particularly at least 1%; and less than 10%, particularly less than 5%, more particularly less than 3%; by weight of the formulation is useful. It is a particular advantage of the emulsion formulation of this invention that the hydroquinone and retinol are sequestered from each other, but can act together upon topical application of the formulation.

Another advantage of the emulsion formulation, according to this invention, is that the free hydroquinone in the formulation enhances the stability of the entrapped or impregnated hydroquinone by preventing or delaying its release from the porous microparticles and micro-agglomerates. At the same time the free hydroquinone at least partially saturates the vehicle to enhance hydroquinone stability, it also is present immediately upon topical application to provide therapeutic benefits. Once the emulsion formulation according to the invention has been placed upon the skin the inhibiting effect of the free hydroquinone is released and hydroquinone from the micro-agglomerates and impregnated porous microparticles become available for therapeutic benefit.

The formulation may also contain additional ingredients such as antioxidants, chelating agents, colorants, fragrances, preservatives, and the like, as necessary or desired, typically in amounts less than 1% by weight of the formulation, as well as suitable thickening agents. Suitable antioxidants and chelating agents are those previously mentioned; with a water-soluble antioxidant for the aqueous phase (especially sodium metabisulfite), and an oil-soluble antioxidant for the organic phase. Suitable preservatives include the parabens, such as methylparaben, propylparaben, isopropylparaben, butylparaben, and isobutylparaben, and their salts such as sodium butylparaben, benzoic acid and its salts and esters, benzyl alcohol, urea derivatives such as diazolidinyl urea, imidazolidinyl urea, and DMDM hydantoin, sorbic acid and its salts, and the like. Suitable colorants and fragrances will be a matter of choice, provided only that they should be compatible with the formulation and the dispensing container.

The oil-in-water emulsion may be prepared by methods well known to the art, typically by mixing the aqueous phase ingredients and the dispersant with heating until a uniform solution or dispersion is obtained (optionally in several stages), mixing the organic phase ingredients with heating until a uniform solution or dispersion is obtained (also optionally in several stages), then adding the aqueous phase to the organic phase with agitation (e.g. stirring or other shearing technique) to form an oil-in-water emulsion of the two phases. These and all other processing steps are typically performed under an inert atmosphere, for example of nitrogen, and all steps involving retinol are performed under yellow light to protect the retinol from exposure to ultraviolet light. The emulsion is cooled with stirring. Once the emulsion is sufficiently cooled, it may be homogenized if necessary. The hydroquinone component (micro-agglomerates and/or porous microparticles) and retinol-impregnated porous microparticles, as well as the temperature-sensitive or volatile ingredients, such as any fragrance, are added and uniformly dispersed in the emulsion, which may be degassed. Finally, storage or dispensing containers are filled with the oil-in-water emulsion.

Suitable creams for this invention are semi-solid oil-in-water emulsions and are generally higher in oil content. They are typified by a relatively heavy consistency. Creams are attractive in that a small amount can be used to cover a comparatively large surface area. Furthermore, creams are easily applied but not easily washed off and, thus, are frequently employed as treatment and protective products. Creams of a heavier variety are formulated for more intensive moisturizing. Such creams are characterized by augmented levels of absorbent and humectant materials.

Creams can be prepared by methods well known in the art (*Chemistry and Technology of the Cosmetics and Toiletries Industry*, 2nd edition, Blackie Academic & Professional (Chapman & Hall), 1996, ch. 1 and 3). They are usually sold in tubes or jars.

Suitable lotions for this invention are oil-in-water emulsions typically containing about 10–15% oil phase and about 85–90% water phase—a higher water phase content than that found in creams. Lotions are attractive formulations in that they flow easily and rub in quickly without leaving behind a feeling of stickiness. They thus provide the ability to hydrate dry skin quickly.

Lotions can be prepared by methods well known in the art (*Chemistry and Technology of the Cosmetics and Toiletries Industry*, 2nd edition, Blackie Academic & Professional (Chapman & Hall), 1996, ch. 1 and 3). Lotions are typically sold in tubes and bottles.

Dispensing Containers

The term "dispensing container" refers to a container suitable for containing the formulations of the first aspect of this invention. Dispensing containers are well known in the packaging art; and suitable containers include tubes (of the kind widely used to hold topical formulations, cosmetics, and the like), airless pumps, sachets or pouches, and the like. Such containers are desirably "barrier containers", which are dispensing containers constructed of materials such that, when filled with the formulation and sealed, they effectively prevent contact of the formulation with atmospheric oxygen and light, and thereby prevent or minimize oxidative or photocatalyzed degradation of the formulation. Desirably, any free space within the dispensing container after it is filled with the desired content of the formulation is filled with an inert gas, such as nitrogen or the rare gases, e.g. argon. A preferred inert gas is nitrogen. Filling a dispensing container with inert gas and sealing it implies that the oxygen is so sufficiently removed and excluded from the container that oxidative degradation of the formulation is minimized.

Barrier containers are well known in the packaging art; and are widely used for the storage of prepackaged materials subject to oxidative or photocatalyzed degradation. Such containers are typically prepared from polymeric co-extrusions in which one or more of the polymer layers is a "barrier polymer", customarily defined as a polymer having an oxygen permeability of less than about 40 $cm^3 \cdot \mu m/(m^2 \cdot d \cdot kPa)$ at 23° C. Barrier polymers and their uses are described, for example, in the article entitled "Barrier Polymers" in The Wiley Encyclopedia of Packaging Technology, M. Baker, Ed., John Wiley and Sons, New York, 1986. Such containers are also typically prepared from foil laminates (polymeric laminates in which one or more of the layers is a metal foil, especially an aluminum foil, or a metallized polymeric layer); and may also contain other non-polymeric layers. Barrier containers may be made in many forms, but those forms particularly applicable to this invention are preformed or form-fill-and-seal sachets or pouches, tubes, airless pumps, and the like. They are fillable and sealable by methods well known to the packaging art; for example, already capped or sealed and capped tubes open at the bottom end are filled from the open end and sealed by any suitable means, typically by heat sealing (heating either by direct conduction, applicable to all materials, or by inductive heating, applicable if a metal foil or foil laminate is present in the area of the container to be sealed).

A particularly convenient dispensing container is a sachet or pouch formed from a foil laminate, as these containers are already widely used as single-dose or sample containers for topical medications or cosmetics and may be conveniently filled with the formulation and sealed by automated packaging machinery.

The invention is illustrated by the following non-limiting Examples. All percents are weight percents unless stated otherwise.

EXAMPLE 1
Hydroquinone Entrapped in Micro-Agglomerates

Hydroquinone entrapped in micro-agglomerates was prepared to the following formulation:

| Ingredient | Weight percent |
| --- | --- |
| Hydroquinone | 60.00 |
| Micro-agglomerates[1] | 36.00 |
| Ascorbic acid | 2.00 |
| Sodium metabisulfite | 2.00 |

[1]The micro-agglomerate used was POLYTRAP ® P020A (Advanced Polymer Systems, Inc. now Enhanced Derm Technologies, Inc. of Redwood, CA), chemical name: lauryl methacrylate/ethylene glycol dimethacrylate crosspolymer micro-agglomerates.

One half of the total hydroquinone was dissolved in ethanol with mixing. A solution of one half of the sodium metabisulfite and one half of the ascorbic acid in deionized water was prepared and added to the hydroquinone solution with mixing. The micro-agglomerates were stirred and purged with nitrogen. The hydroquinone/ascorbic acid/sodium metabisulfite solution was blended in under a nitrogen blanket, and the resulting mixture was dried under vacuum. The second half of the hydroquinone/ascorbic acid/sodium metabisulfite solution was then prepared, added to the dried product, and blended under a nitrogen blanket. The final product was dried under vacuum to specified volatile and ethanol content. The hydroquinone-loaded micro-agglomerates were stored under a nitrogen atmosphere.

EXAMPLE 2
Retinol-Impregnated Microparticles, 22.5%

Retinol-impregnated microparticles were prepared to the following formulation:

| Ingredient | Weight percent |
| --- | --- |
| Retinol blend[1] | 47.000 |
| Microparticles[2] | 51.931 |
| Tocopheryl acetate | 1.000 |
| Ascorbic acid | 0.023 |
| Disodium EDTA | 0.023 |
| Propyl gallate | 0.023 |

[1]The retinol blend contained approximately 45.0% retinol, 51.25% polysorbate 20, 3.0% BHT, and 0.75% BHA.
[2]The microparticles used were Microsponge ® (Advanced Polymer Systems, Inc. now Enhanced Derm Technologies, Inc. of Redwood, CA), chemical name: porous methyl methacrylate/ethylene glycol dimethacrylate crosspolymer microparticles, having a weight average particle diameter of 20 µm, a surface area of 225 m$^2$/g, and a pore volume of 1 cm$^3$/g.

Under yellow light, the retinol blend, tocopheryl acetate, ascorbic acid, disodium EDTA, and propyl gallate were dissolved in isopropanol, using 50 g isopropanol per 50 g of retinol blend. The resulting solution was purged with nitrogen and was mixed with the microparticles, agitating until the solution was absorbed. Once the solution had been fully absorbed by the microparticles, the solvent was removed under vacuum, and the impregnated microparticles were stored in brown glass jars or opaque packets under a nitrogen atmosphere.

EXAMPLE 3
Formulation Containing Hydroquinone, 2% (Entrapped in Micro-Agglomerates) and Retinol, 0.3% (Impregnated in Microparticles, 20% Overage) in an Oil-in-Water Emulsion An oil-in-water formulation of the invention was prepared with the following ingredients:

| Ingredient | Weight percent |
| --- | --- |
| Part I | |
| DI water | 61.127 |
| Magnesium Aluminum Silicate (Veegum Regular) | 0.50 |
| Glycerin 99.7% | 3.00 |
| Methylparaben NF (Methylparaben) | 0.40 |
| Sodium Metabisulfite | 1.00 |
| Edetate Disodium, USP (Sequestrene NA2) | 0.20 |
| Triethanolamine 99% | 0.30 |
| Part II | |
| Cetyl Ricinoleate (Naturchem CR) | 2.00 |
| $C_{10}$–$C_{30}$ Cholesterol/Lanosterol Esters (Super Sterol Ester)- | 2.50 |
| Cetyl Alcohol NF (Crodacol C95) | 2.00 |
| Emulsifying wax, NF (Polawax) | 4.50 |
| Dimethicone (DC 200, 350 cst) | 2.00 |
| Vitamin E, USP (acetate) | 0.10 |
| PEG-10 Soya Sterol (Generol 122E-10) | 0.50 |
| Stearic Acid, NF (Emersol 132) | 0.50 |
| Butylated Hydroxy Toluene, NF | 0.10 |
| Cyclomethicone (DC 345 Fluid) | 1.00 |
| Caprylic/Capric Triglyceride (Myritol 318) | 6.00 |
| DEA-Cetyl Phosphate (Amphisol) | 1.00 |
| Ascorbyl palmitate | 0.05 |
| Part III | |
| Hydroquinone entrapment, 60% (from Example 1) | 3.34 |
| Part IV | |
| DI water | 2.55 |
| Retinol-impregnated microparticles, 22.5% (from Example 2) | 1.80 |
| Part V | |
| Alpha-bisabolol | 0.083 |
| Part VI | |
| Benzyl Alcohol, NF | 1.00 |
| Phenoxyethanol | 0.50 |
| Polyacrylamide (and) $C_{13-14}$ isoparaffin (and) laureth 7 (Sepigel 305) | 1.95 |

The water of Part I was weighed in a suitable container and heated while mixing; the remaining ingredients of Part I were then added, forming the aqueous phase. In a separate container, all of the ingredients of Part II were weighed and heated until the solution became clear, forming the oil phase. Part II was added to Part I with good mixing, forming an oil-in-water emulsion. The heat was then shut off, and Part III, the premix of Part IV, Part V, and the ingredients of Part VI were added sequentially with good mixing. Purging with nitrogen occurred throughout the manufacturing process. The formulation was packaged in Glaminate tubes.

EXAMPLE 4

Stability Data of Entrapped vs. "Free" Hydroquinone Formulations

To demonstrate the benefits of the invention, the formulation of Example 3 was compared to a similar formulation in which the 2% hydroquinone was present "free" in the emulsion rather than entrapped in micro-agglomerates. The two formulations were packaged in Glaminate tubes, and samples were taken for analysis after storage under defined conditions.

| | Active Ingredient Content, % | | | |
|---|---|---|---|---|
| | Example 3 | | Comparative formulation | |
| Storage conditions | Hydro-quinone entrapped | Retinol impregnated | Hydro-quinone free | Retinol impregnated |
| Initial | 2.00 | 0.37 | 2.02 | 0.35 |
| One month at 40° C. | 2.03 | 0.32 | 1.80 | 0.34 |
| One month at 45° C. | 2.07 | 0.31 | 1.80 | 033 |
| Two months at 40° C. | 2.00 | 0.33 | | |
| Three months at 40° C. | 2.10 | 0.31 | | |

The formulation with "free" hydroquinone showed approximately 10% loss of hydroquinone potency and slight physical separation at 40° C., and very bad separation at 45° C. after one month, whereas the formulation of the invention was physically and chemically stable after three months at 40° C.

EXAMPLE 5

An oil-in-water formulation, according to the invention, was prepared using a process similar to that described in Example 3. The following is a list of ingredients:

| Hydroquinone 4% and Retinol 0.15% (20% Overage) Cream | |
|---|---|
| Raw Materials | % w/w |
| Purified Water, USP | 61.394 |
| Magnesium Aluminum Silicate | 0.500 |
| Glycerin | 3.000 |
| Triethanolamine, 99% | 0.390 |
| Edetate Disodium | 0.200 |
| Methylparaben | 0.200 |
| Sodium Metabisulfite | 0.300 |
| Cetyl Ricinoleate | 2.000 |
| C10–30 Cholesterol/Lanosterol Esters | 2.500 |
| Cetyl Alcohol | 2.000 |
| Emulsifying Wax | 4.500 |
| Dimethicone | 3.000 |
| PEG-10 Soy Sterol | 0.500 |
| Triethanolamine Stearate | 0.800 |
| dl-alpha Tocopheryl Acetate | 0.100 |
| Ascorbyl Palmitate | 0.050 |
| Butylated Hydroxy Toluene | 0.100 |
| Cyclomethicone (Dow Coming 345 Fluid) | 1.000 |
| Caprylic/Capric Triglyceride (Myritol 318) | 6.500 |
| Cetyl Phosphate (Amphisol A) | 1.000 |
| Polyacrylamide (and) C13–14 Isoparaffin (and) Laureth-7 (Sepigel 305) | 1.950 |
| Hydroquinone, USP (Free) | 1.500 |
| Methyl Methacrylate/Glycol Dimethacrylate Crosspolymer (and) Hydroquinone (and) Ascorbic Acid (and) Sodium Metabisulfite (MICROSPONGE ® P020A Hydroquinone) (Hydroquinone @ 60%) | 4.167 |
| Methyl Methacrylate/Glycol Dimethacrylate Crosspolymer (and) Retinol (and) Tocopheryl Acetate (and) Ascorbic Acid (and) Disodium EDTA (and) Propyl Gallate (and) Polysorbate 20 (and) BHT (MICROSPONGE ® C116A Retinol Blend) (Retinol @ 23.5%) | 0.766 |
| Bisabolol | 0.083 |
| Benzyl Alcohol | 1.000 |
| Phenoxyethanol | 0.500 |
| Total | 100.000 |

To demonstrate the benefits of the invention, the formulation was subjected to a stability study. In a fashion similar to Example 4, the formulation was packaged in a one ounce Glaminate tube. Samples were taken for analysis after storage under the defined conditions.

| | Active Ingredient Content, % by weight Example 5 | |
|---|---|---|
| Storage conditions | Hydroquinone content | Retinol content |
| Initial | 4.02 | 0.19 |
| One month at 5° C. | 3.89 | 0.19 |
| One month at Ambient | 3.95 | 0.19 |
| One month at 30° C. | 3.93 | 0.18 |
| One month at 40° C. | 3.83 | 0.17 |
| Two months at 5° C. | 3.96 | 0.18 |
| Two months at Ambient | 3.90 | 0.17 |
| Two months at 30° C. | 3.86 | 0.18 |
| Two months at 40° C. | 3.93 | 0.16 |
| Three Months at 5° C. | 3.92 | 0.17 |
| Three Months at Ambient | 3.80 | 0.16 |
| Three Months at 30° C. | 3.89 | 0.16 |
| Three Months at 40° C. | 3.89 | 0.14 |
| Six Months at 5° C. | 3.90 | 0.16 |
| Six Months at Ambient | 3.91 | 0.16 |
| Six Months at 30° C. | 4.04 | 0.15 |
| Six Months at 40° C. | 3.88 | 0.12 |

INDUSTRIAL APPLICABILITY

There is presently a need in the dermatological industry for improved compositions to assist in the maintenance, repair and beautification of the human epidermis. The present invention provides a novel oil-in-water emulsion formulation that utilizes the well-recognized and efficacious skin-lightening agent hydroquinone. One limitation of hydroquinone is its instability in formulations for topical application. It is known that over a period of time the hydroquinone content of the formulations will decrease and will become less efficacious. One aspect of the present invention resides in the discovery that enhanced hydroquinone stability can be achieved when the hydroquinone is entrapped in micro-agglomerates and/or impregnated porous microparticles. Further, it has been shown that the presence of small levels of free hydroquinone in the oil-in-water emulsion formulation further enhances the stability of the hydroquinone.

When the hydroquinone is combined with retinol a particularly effective formulation is achieved. Retinol has enjoyed increasing popularity as an active ingredient in skin-care compositions, especially for photo-aging and sun damage. Thus, a combination of hydroquinone which produces a reversible de-pigmentation of the skin and retinol could be found useful and desirable by many patients. The composition and methods of the present invention have enhanced the state of the art and will be readily accepted by clinicians and the consuming public.

While this invention has been described in conjunction with specific embodiments and examples, it will be evident to one of ordinary skill in the art, having regard to this disclosure, that equivalents of the specifically disclosed materials and techniques will also be applicable to this invention; and such equivalents are intended to be included within the following claims.

What is claimed is:

1. An oil-in-water emulsion formulation containing hydroquinone and retinol, comprising:
   (i) an oil-in-water emulsion containing at least 0.01% by weight free hydroquinone; and (ii) separately dispersed within the oil-in-water emulsion,
   (a) one or both of hydroquinone entrapped in micro-agglomerates and hydroquinone-impregnated porous microparticles; and
   (b) retinol-impregnated porous microparticles.

2. The formulation of claim 1, where the total hydroquinone content of the emulsion is from about 0.01% to about 10% by weight.

3. The formulation of claim 2, where the total hydroquinone content of the emulsion is from about 0.1% to about 5% by weight.

4. The formulation of claim 1, where at least a part of the hydroquinone is present entrapped in micro-agglomerates.

5. The formulation of claim 1 where the micro-agglomerates comprise a cross-linked polymer selected from the group consisting of a styrene/divinylbenzene crosspolymer, a vinyl stearate/divinylbenzene crosspolymer, a methyl methacrylate/ethylene glycol dimethacrylate crosspolymer, and a lauryl methacrylate/ethylene glycol dimethacrylate crosspolymer.

6. The formulation of claim 5, where the micro-agglomerates comprise a lauryl methacrylate/ethylene glycol dimethacrylate crosspolymer.

7. The formulation of claim 1, where at least a part of the hydroquinone is present in hydroquinone-impregnated porous microparticles.

8. The formulation of claim 1, where the retinol content of the emulsion is from about 0.0001% to about 10% by weight.

9. The formulation of claim 8, where the retinol content is from about 0.001% to about 5% by weight.

10. The formulation of claim 1, where the porous microparticles have a weight average diameter less than 50 μm.

11. The formulation of claim 10, where the porous microparticles have a weight average diameter of about 20 μm.

12. The formulation of claim 1, where the porous microparticles comprise a cross-linked polymer selected from the group consisting of a styrene/divinylbenzene crosspolymer, a vinyl stearate/divinylbenzene crosspolymer, a methyl methacrylate/ethylene glycol dimethacrylate crosspolymer, and a lauryl methacrylate/ethylene glycol dimethacrylate crosspolymer.

13. The formulation of claim 12, where the porous microparticles comprise a methyl methacrylate/ethylene glycol dimethacrylate crosspolymer.

14. The formulation of claim 1, further comprising at least one additional component selected from an antioxidant, a chelating agent, a colorant, a fragrance, and a preservative.

15. A method of simultaneous application of hydroquinone and retinol to the skin, comprising topically applying the formulation of claim 1.

16. The method of claim 15, where the total hydroquinone content of the emulsion is from about 0.01% to about 10% by weight.

17. The method of claim 16, where the hydroquinone content of the emulsion is from about 0.1% to about 5% by weight.

18. The method of claim 15, where the retinol content of the emulsion is from about 0.0001% to about 10% by weight.

19. The method of claim 18, where the retinol content of the emulsion is from about 0.001% to about 5% by weight.

20. The method of claim 15, where at least a part of the hydroquinone is present entrapped in micro-agglomerates.

21. The method of claim 15, where at least a part of the hydroquinone is present in hydroquinone-impregnated porous microparticles.

* * * * *